United States Patent
Roberts

(10) Patent No.: US 11,317,854 B1
(45) Date of Patent: May 3, 2022

(54) TRIGGER POINT TREATMENT METHOD, SYSTEM, AND DEVICE FOR NEUROMUSCULOSKELETAL PAIN

(71) Applicant: PSOAS Massage Therapy Offices, P. C., New York, NY (US)

(72) Inventor: Michelle G. Roberts, New York, NY (US)

(73) Assignee: PSOAS Massage Therapy Offices, P. C., New York, NY (US)

( * ) Notice: Subject to any disclaimer, the term of this patent is extended or adjusted under 35 U.S.C. 154(b) by 875 days.

(21) Appl. No.: 16/157,407

(22) Filed: Oct. 11, 2018

Related U.S. Application Data

(60) Provisional application No. 62/571,528, filed on Oct. 12, 2017.

(51) Int. Cl.
| | |
|---|---|
| *A61H 39/02* | (2006.01) |
| *A61B 5/00* | (2006.01) |
| *A61B 8/00* | (2006.01) |

(52) U.S. Cl.
CPC .......... *A61B 5/4519* (2013.01); *A61B 5/0033* (2013.01); *A61B 5/4824* (2013.01); *A61B 8/4405* (2013.01); *A61B 8/4427* (2013.01); *A61H 39/02* (2013.01); *A61B 2560/0406* (2013.01); *A61H 2201/0157* (2013.01)

(58) Field of Classification Search
CPC .... A61H 39/00; A61H 39/002; A61H 39/007; A61H 39/02; A61H 39/04
See application file for complete search history.

(56) References Cited

U.S. PATENT DOCUMENTS

| | | | |
|---|---|---|---|
| 654,983 | A | 5/1907 | Clark |
| 3,710,785 | A | 1/1973 | Hilger |
| 4,669,452 | A | 6/1987 | Osawa |
| 5,063,911 | A | 11/1991 | Teranishi |
| 5,065,743 | A | 11/1991 | Sutherland |
| 5,103,809 | A | 4/1992 | DeLuca et al. |
| 5,113,847 | A * | 5/1992 | Holzworth ............ A61H 7/00 128/907 |
| 5,183,034 | A | 2/1993 | Yamasaki et al. |
| 5,352,188 | A | 10/1994 | Vitko |
| 5,356,369 | A | 10/1994 | Yamasaki et al. |
| 5,445,647 | A * | 8/1995 | Choy ............... A61H 39/04 128/101.1 |
| 5,899,868 | A | 5/1999 | VandeBerg |
| 6,010,467 | A | 1/2000 | Smith |
| 6,267,738 | B1 | 7/2001 | Louis |
| 7,153,282 | B1 | 12/2006 | Dudley |
| 9,782,324 | B2 * | 10/2017 | Crunick ............ A61N 1/328 |
| 10,016,337 | B2 | 7/2018 | Roberts et al. |

(Continued)

*Primary Examiner* — LaToya M Louis
(74) *Attorney, Agent, or Firm* — Olav M. Underdal; IDP Patent Services

(57) ABSTRACT

A trigger point treatment system for treating a patient, includes a cart, including a display; a trigger point scanning device with a scanning probe, and a trigger point massage therapy device, including a pressure point tip, a pressure sensor component, and an actual pressure indicator. A method of trigger point treatment includes scanning for myofascial trigger points, including locating, mapping, and marking trigger points; measuring a pressure pain threshold; applying a massage treatment; and optionally applying an injection treatment.

12 Claims, 15 Drawing Sheets

(56) References Cited

U.S. PATENT DOCUMENTS

| | | | |
|---|---|---|---|
| 2002/0055092 A1* | 5/2002 | Hochman | G01N 33/6896 435/4 |
| 2005/0143777 A1* | 6/2005 | Sra | G06T 17/00 607/4 |
| 2005/0177202 A1* | 8/2005 | Classen | A61N 1/40 607/46 |
| 2007/0106342 A1* | 5/2007 | Schumann | A61N 1/36021 607/46 |
| 2007/0129759 A1* | 6/2007 | Colthurst | A61N 1/32 607/2 |
| 2007/0270727 A1* | 11/2007 | Khorassani Zadeh | A61H 1/008 601/120 |
| 2008/0139981 A1 | 6/2008 | Walquist et al. | |
| 2015/0080990 A1* | 3/2015 | Crunick | A61D 1/00 607/101 |
| 2015/0119771 A1* | 4/2015 | Roberts | A61N 1/26 601/135 |
| 2017/0086785 A1* | 3/2017 | Bjaerum | A61B 8/13 |
| 2019/0008410 A1* | 1/2019 | Crosson | A61B 5/053 |
| 2019/0053979 A1* | 2/2019 | Han | G16H 20/30 |
| 2019/0142337 A1* | 5/2019 | Hazelwood | A61B 8/461 600/438 |
| 2019/0175097 A1* | 6/2019 | Cowie | A61B 5/7455 |

* cited by examiner

Trigger Point Treatment System

Trigger Point Scanning Device

722

722

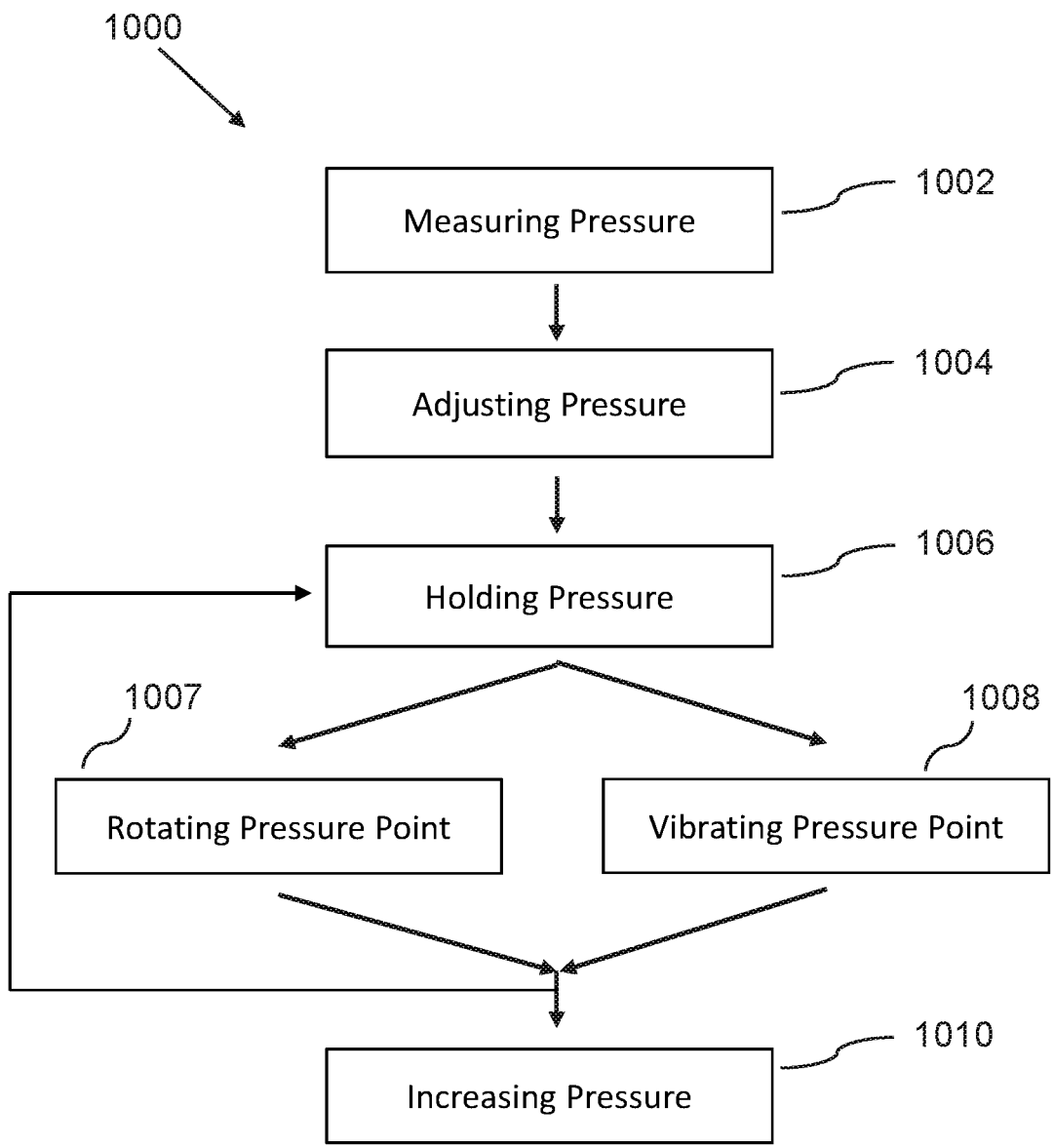

TRIGGER POINT TREATMENT METHOD, SYSTEM, AND DEVICE FOR NEUROMUSCULOSKELETAL PAIN

CROSS-REFERENCE TO RELATED APPLICATIONS

This application claims the benefit of U.S. Provisional Application No. 62/571,528, filed Oct. 12, 2017; which is hereby incorporated herein by reference in its entirety.

FIELD OF THE INVENTION

The present invention relates generally to the field of devices and methods for trigger point and neuromusculoskeletal pain therapy, and herein particularly methods, systems, and devices that allows for a more efficient way for a practitioner to locate and map trigger points, measure pain threshold, and treat myofascial trigger points.

BACKGROUND OF THE INVENTION

Trigger points, also known as trigger sites or muscle knots, are hyperirritable spots in skeletal muscle that are associated with palpable nodules in taut bands of muscle fibers.

Trigger points will often cause otherwise unexplained pain that radiates from such points of local tenderness to related areas, sometimes not immediately adjacent to the trigger point itself.

Trigger points are caused by muscle exertion, overuse, repetitive stress, bio-mechanical and postural overload. Overload is when a muscle is placed in an over shortened or overstretched state for a prolonged period of time. Deep thumb or elbow pressure is applied to relief muscular pain and dysfunction causing the trigger points to deactivate.

A trigger point is described as a clinical finding with the following symptoms:
 a) Pain related to a discrete, irritable point in skeletal muscle or fascia, not caused by acute local trauma, inflammation, degeneration, neoplasm or infection.
 b) The painful point can be felt as a nodule or band in the muscle, and a twitch response can be elicited on stimulation of the trigger point.
 c) Palpation of the trigger point reproduces the patient's complaint of pain, and the pain radiates in a distribution typical of the specific muscle harboring the trigger point.
 d) The pain cannot be explained by findings on neurological examination.

Pain management health professionals, such as neurologist, physiatrist, osteopaths, orthopedic doctors, chiropractors, occupational therapists, physical therapists, acupuncturists, and massage therapists can identify trigger points as the cause of radiating or localized pain, and initiate various related treatment regimes.

The most common treatment approach for trigger point is trigger point therapy/ischemic compression. A practitioner or therapists will palpate the muscle groups to locate a trigger point and treat the area often using thumb, elbows, or simple manual assisted tools, such as: THERA CANE®, KNOBBLE®, QFLEX™ acupressure sticks or ACUFORCE®, to apply pressure directly upon the trigger point, in order to reduce strain on their hands.

Healthcare practitioner/therapist will often develop joint tenderness and injuries to hands and fingers as a consequence of long-term treatment of patients, due to the reactive forces and pressure manifesting in the arms, elbows, hands and fingers of the practitioner during trigger point treatment sessions.

The benefits of trigger point therapy include:
 a) Aids in deactivating trigger points;
 b) Reduces muscle contraction and muscle spasm;
 c) Reduces muscle overload and pain patterns
 d) Reduces inflammation, adhesion and nodules;
 e) Restores muscle function and regeneration;
 f) Increases muscle length, flexibility and elasticity
 g) Increases motor function and range of motion; and
 h) Increases blood flow, muscle relaxation and nutrients to localized areas.

The results of manual therapy are related to the skill level of the therapist. If trigger points are pressed for too short a time, they may activate or remain active; if pressed too long or hard, they may be irritated, or the muscle may be bruised, resulting in pain in the area treated. Additionally, a practitioner has to rely on palpating a muscle group to find a trigger point and the point can be often missed if the site is not palpated accurately.

As such, considering the foregoing, it may be appreciated that there continues to be a need for novel and improved physiotherapeutic devices and methods for treatment of trigger points.

SUMMARY OF THE INVENTION

The foregoing needs are met, to a great extent, by the present invention, wherein in aspects of this invention, enhancements are provided to the existing model of trigger point therapy In an aspect, a trigger point treatment system can include:
 a) a system body, which can be a cart or a desktop unit, including:
  a display;
 b) a trigger point scanning device, which can be connected to the system body, the trigger point scanning device including:
  a scanning probe, such that the scanning probe can be configured to receive a scanning signal from a treatment area of the patient, such that the trigger point scanning device processes the scanning signal to generate a scanning image, which is transmitted to the display; and
 c) a trigger point massage therapy device, including:
  a pressure point tip;
  a pressure sensor component, which can be connected to the pressure point tip, such that the pressure sensor component measures a pressure applied to the pressure point tip;
  an actual pressure indicator, which can display a current actual pressure, obtained in communication with the pressure sensor component;
  wherein the trigger point massage therapy device can be configured to store a plurality of trigger points, with a location and a maximum pressure for each trigger point in the plurality of trigger points;
 whereby a therapist applies an applied pressure to the treatment area of the patient via the pressure point tip, such that the therapist adjusts the applied pressure via observation of the current actual pressure on the actual pressure indicator.

In a related aspect, the trigger point massage therapy device can be configured to receive a manual signal from the patient to indicate that the applied pressure is painful, such that the maximum pressure is the applied pressure when the patient submits the manual signal, such that the maximum pressure is stored in the trigger point massage therapy device for each trigger point in the plurality of trigger points.

In a further related aspect, the trigger point treatment system can further include a signal device, which comprises a signal button; such that the signal device is connected to the trigger point massage therapy device; such that the patient provides the manual signal by pressing the signal button.

In a related aspect, the scanning probe can be an ultrasound imaging scanning probe.

In another related aspect, the trigger point massage therapy device can further include a target pressure indicator, which displays a targeted pressure, wherein the targeted pressure is determined as a predetermined proportion of the maximum pressure.

In a further related aspect, the predetermined proportion can be in a range of 5%-95%.

In an aspect, a method of trigger point treatment for a healthcare practitioner to treat a patient can include:
  a) scanning for myofascial trigger points, by using a trigger point scanning device, including:
    i. locating trigger points by using the trigger point scanning device to identify a plurality of trigger points by reviewing scanning images on a display;
    ii. mapping trigger points, wherein a location can be obtained from a scanner location sensor for each of the trigger points, such that the location can be displayed with a location marking on a three-dimensional anatomical model shown on the display; and
    iii. marking trigger points, wherein each trigger point is marked with a physical marking on the patient;
  b) measuring a pressure pain threshold for each located trigger point in the plurality of trigger points by using a trigger point massage therapy device, by gradually increasing an actual pressure until the patient submits a manual signal to indicate that the pressure is painful, such that a maximum pressure is the actual pressure when the patient submits the manual signal, such that the maximum pressure is stored in the trigger point massage therapy device for each located trigger point;
  c) applying a trigger point treatment for each located trigger point by using a trigger point massage therapy device, such that an actual/targeted treatment pressure can be applied for each located trigger point as a predetermined proportion of the maximum pressure; and
  d) (optionally) applying an injection treatment for each located trigger point by injecting a treatment liquid into each located trigger point.

In a related aspect, the healthcare professional can input patient data, name, address, insurance identification number, date of birth, age, sex, pain scale, type of pain such as acute, moderate or chronic.

In a related aspect, the healthcare practitioner can use the trigger point treatment system to locate and treat trigger points on body zones, including scalp and neck, cervical regions, the thoracic region, the lumbar region, the pelvis region, and upper and lower extremities.

In an aspect, a trigger point massage therapy device can include a main body with a soft palm pressure pad, a pressure point tip for application of pressure to a patient, and a handle with rubberized grip points, whereby a therapist can apply well-controlled pressure with one or two-handed operation.

In a related aspect, the therapist can employ functions to monitor the applied pressure and compare that to a target pressure level.

In a related aspect, the trigger point massage therapy device can apply rotation, pulsation, vibration and forward/backward tip movement, which can increase or decrease applied pressure in increments of a predetermined duration, specified in milliseconds.

In further related aspects, the device can also provide heating, cold laser light, infrared, ultrasound, electrical stimulation, and other common therapeutic methods and functions.

In a related aspect, a method for trigger point massage therapy can include measuring a pressure, adjusting the pressure, holding the pressure, rotating/unwinding and/or vibrating, and increasing the pressure.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 16 is a schematic diagram of a method or process for trigger point massage therapy, according to an embodiment of the invention.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

Neurologists, Physiatrists, Chiropractors, Physical Therapists, Massage Therapists and Acupuncturists rely on their fingers/hands to identify trigger points and can often palpate the wrong location of trigger points or missed the location of several trigger points. The methods and system disclosed herein allows for a more efficient way for a practitioner to locate, map, mark, measure pain threshold, and treat myofascial trigger points.

Figure 1:
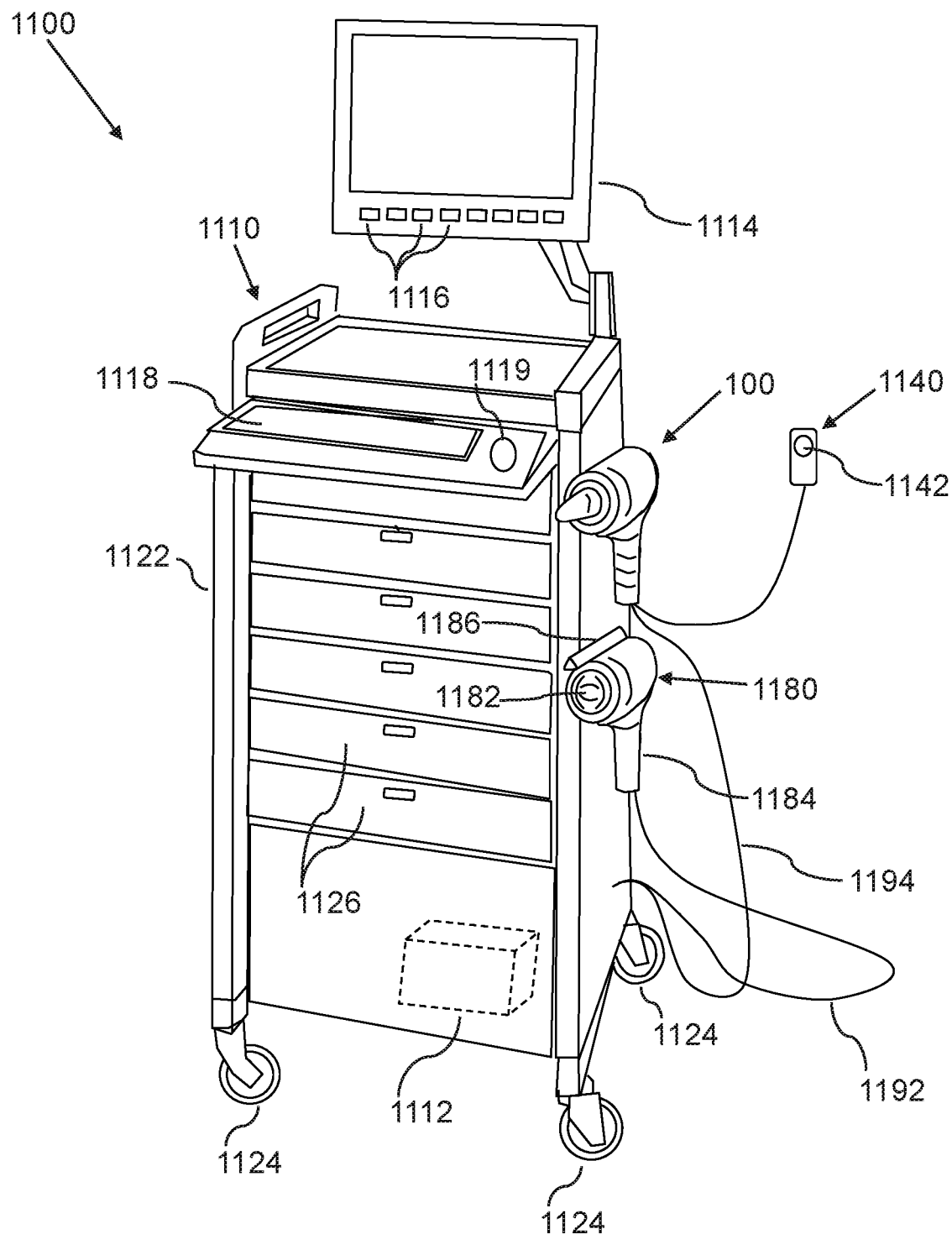
FIG. 1 is a perspective view of a trigger point treatment system, according to an embodiment of the invention.
Figure 7:
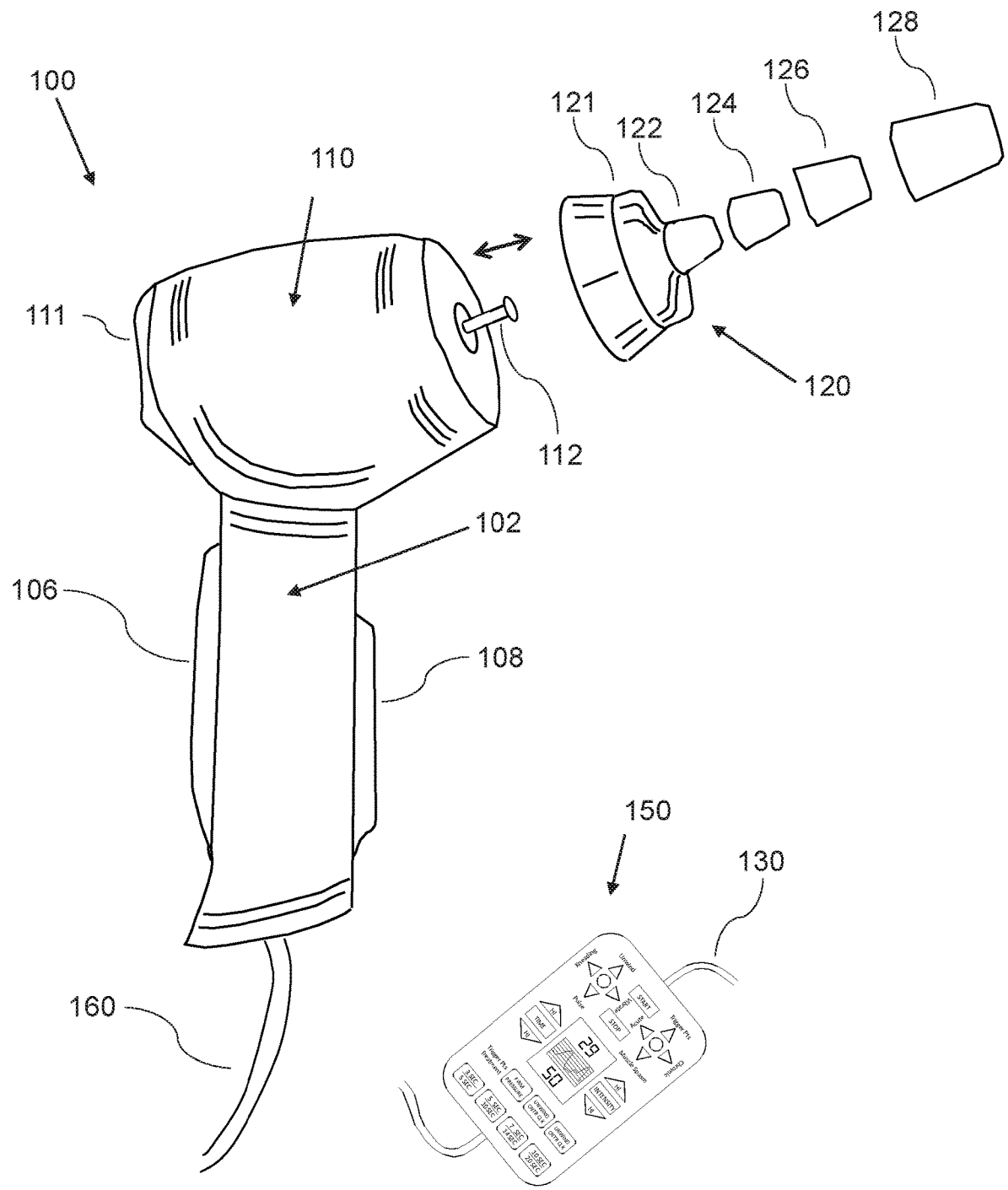
FIG. 7 is a perspective view of a trigger point massage therapy device, according to an embodiment of the invention.
Figure 8:
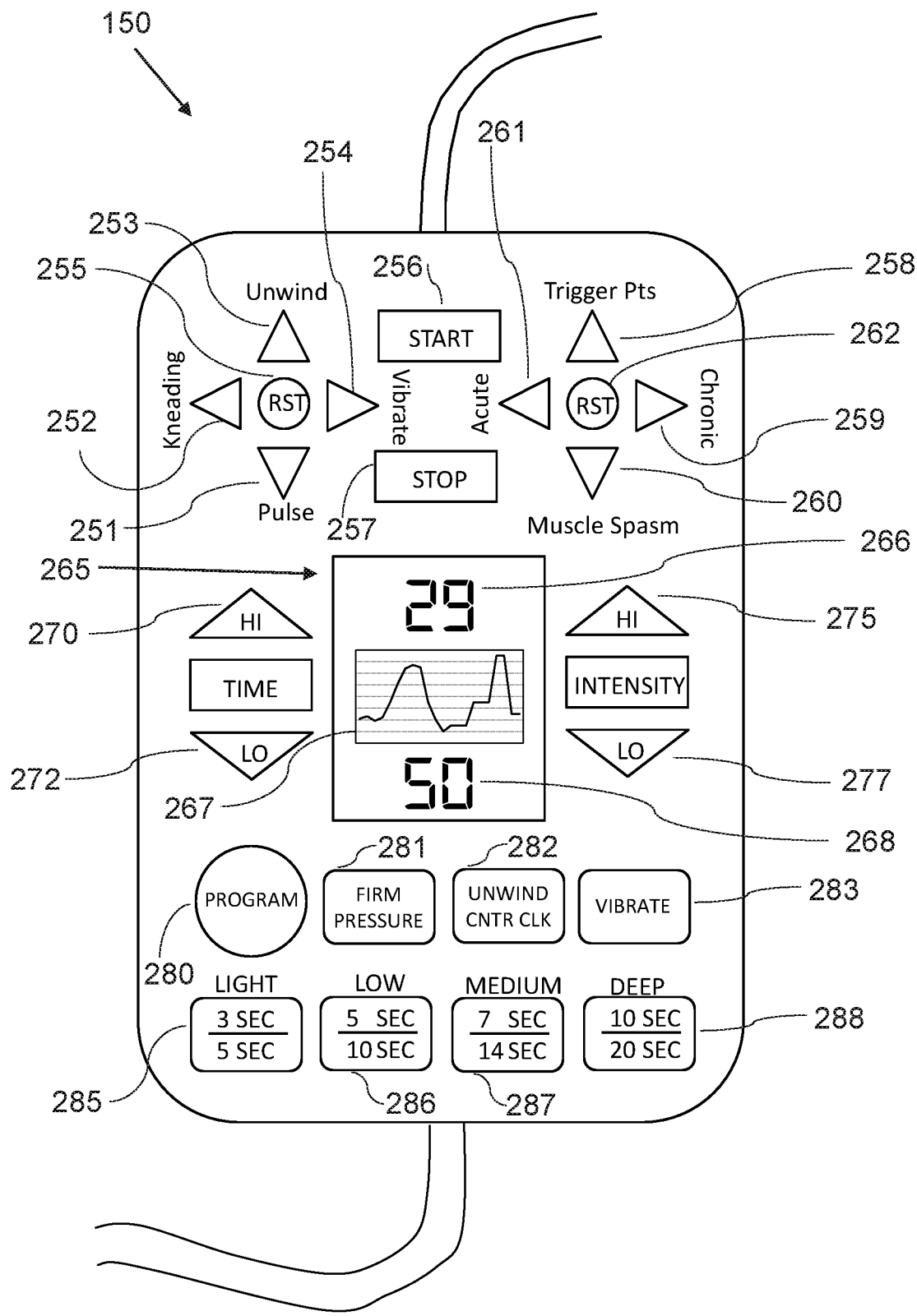
FIG. 8 is a front view of a control unit of a trigger point massage therapy device, according to an embodiment of the invention.
Figure 9:
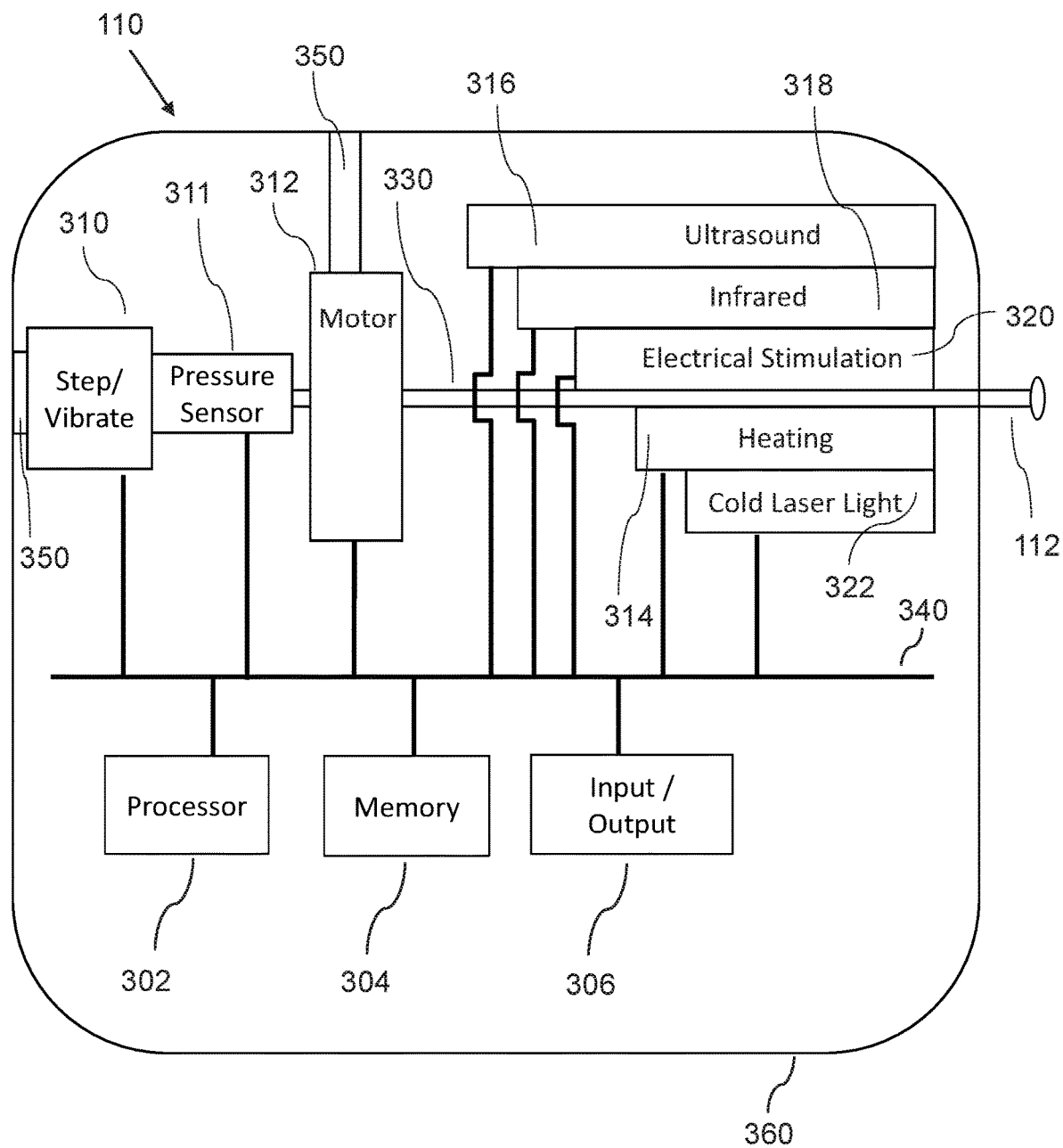
FIG. 9 is a schematic diagram of a trigger point massage therapy device, according to an embodiment of the invention.

In an embodiment, a trigger point treatment system 1100 can include:
 a) a system body 1110, which can be cart 1110, which system body/cart 1110 can include:
    i. a main control unit 1112, which can be configured to program and control functions of the trigger point treatment system 1100;
    ii. a display 1114, which can have touch capability;
    iii. optionally, control buttons 1116;
    iv. optionally, a keyboard 1118, which can be retractable and can have inbuilt track ball 1119;
    v. a cart body 1122;
    vi. wheels 1124;
    vii. Drawers 1126, which can be open trays 1126;
 b) a trigger point scanning device 1180, which is connected to the cart 1110, such that the trigger point scanning device 1180 can include:
    i. a scanning probe 1182, which can be an ultrasound imaging scanning probe 1182, such that the scanning probe 1182 is configured to receive a scanning signal from a treatment area 1226 of the patient 1224, such that the trigger point scanning device 1180 processes the scanning signal to generate a scanning image (i.e. an ultrasound image), which is transmitted to the display 1114 such that the scanning probe 1182 transmits an ultrasound image for display on the display 1114 of the cart 1110, which can be in transmission via the main control unit 1112 or sent directly to the display 1114. The trigger point scanning device 1180 can use well-known methods of ultrasound sonography to generate a scanning image, but can also be based on other medical imaging technology, such as radiography, magnetic resonance imaging, photoacoustic imaging, functional near-infrared spectroscopy, etc.;
    ii. a probe handle 1184, which can be a pistol-type grip 1184 or some other ergonomic handle configuration, which can be manufactured in plastic or other suitable material;
 c) a trigger point massage therapy device 100, as shown in FIGS. 1 and 7, which can include:
    i. a main body 110;
    ii. a pressure point tip 122;
    iii. a pressure sensor component 311, as shown in FIG. 9, which is connected to the pressure point tip 122, such that the pressure sensor component measures a pressure applied to the pressure point tip;
    iv. an actual pressure indicator 266, as shown in FIG. 8, which displays a current actual pressure, obtained in communication with the pressure sensor component;
    v. a handle 102, which is connected to the main body; whereby a therapist 1222 holds the handle 102, to apply an applied pressure to a treatment area 1226 of a patient 1224 via the pressure point tip 122, such that the therapist 1222 adjusts the applied pressure via observation of the current actual pressure on the actual pressure indicator 266.

In a related embodiment, the system body 1110 can be configured as a desktop system body 1110 for positioning on a table, such that it typically does not include wheels.

In various embodiments, the trigger point treatment system 1100 can be manufactured in consumer, prosumer/semi-professional, and professional variants for use in both home and clinical environments.

In various embodiments, the trigger point treatment system 1100 can provide a more efficient treatment method for healthcare providers while offering a direct treatment mechanism with well-controlled electromechanical ischemic compression friction therapy (ICFT) application using Ischemic Compression Technology (ICT) to treat myofascial trigger point.

In another related embodiment, the trigger point scanning device 1180 can be connected to the system body 1110 (and to the control unit 1112) with a first power and control cable 1192, and the trigger point massage therapy device 100 can be connected to the system body 1110 (and to the control unit 1112) with a second power and control cable 1194.

Figure 4:
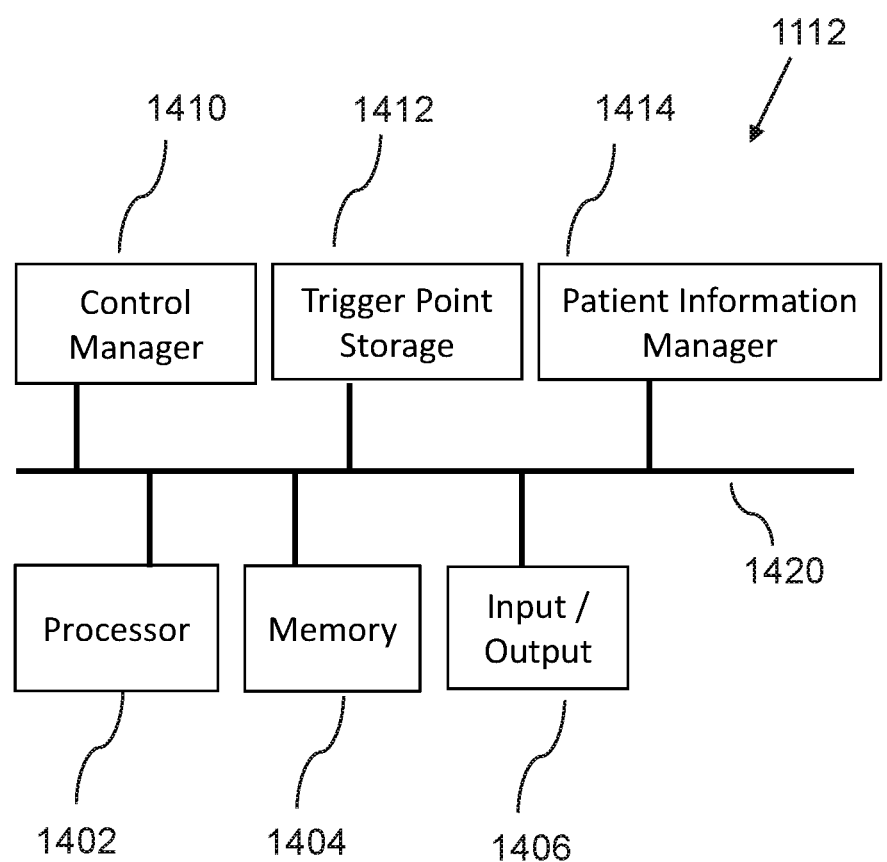
FIG. 4 is a schematic diagram of a main control unit of a trigger point treatment system, according to an embodiment of the invention.

In another related embodiment, as shown in FIG. 4, the main control unit 1112 can include:
 a) A processor 1402;
 b) A non-transitory memory 1404;
 c) An input/output component 1406;
 d) A control manager 1410, which can be configured to communicate with and control operation of the trigger point scanning device 1180 and the trigger point massage therapy device 100;

e) a trigger point storage 1412, which can be configured to store and process information related to identified trigger points, such that the trigger point storage 1412 can be configured to store a plurality of trigger points, with a location and a maximum pressure for each trigger point in the plurality of trigger points; and f) a patient information manager 1414, which can be configured to store and process patient information; all connected via g) a data bus 1420.

Figure 2:
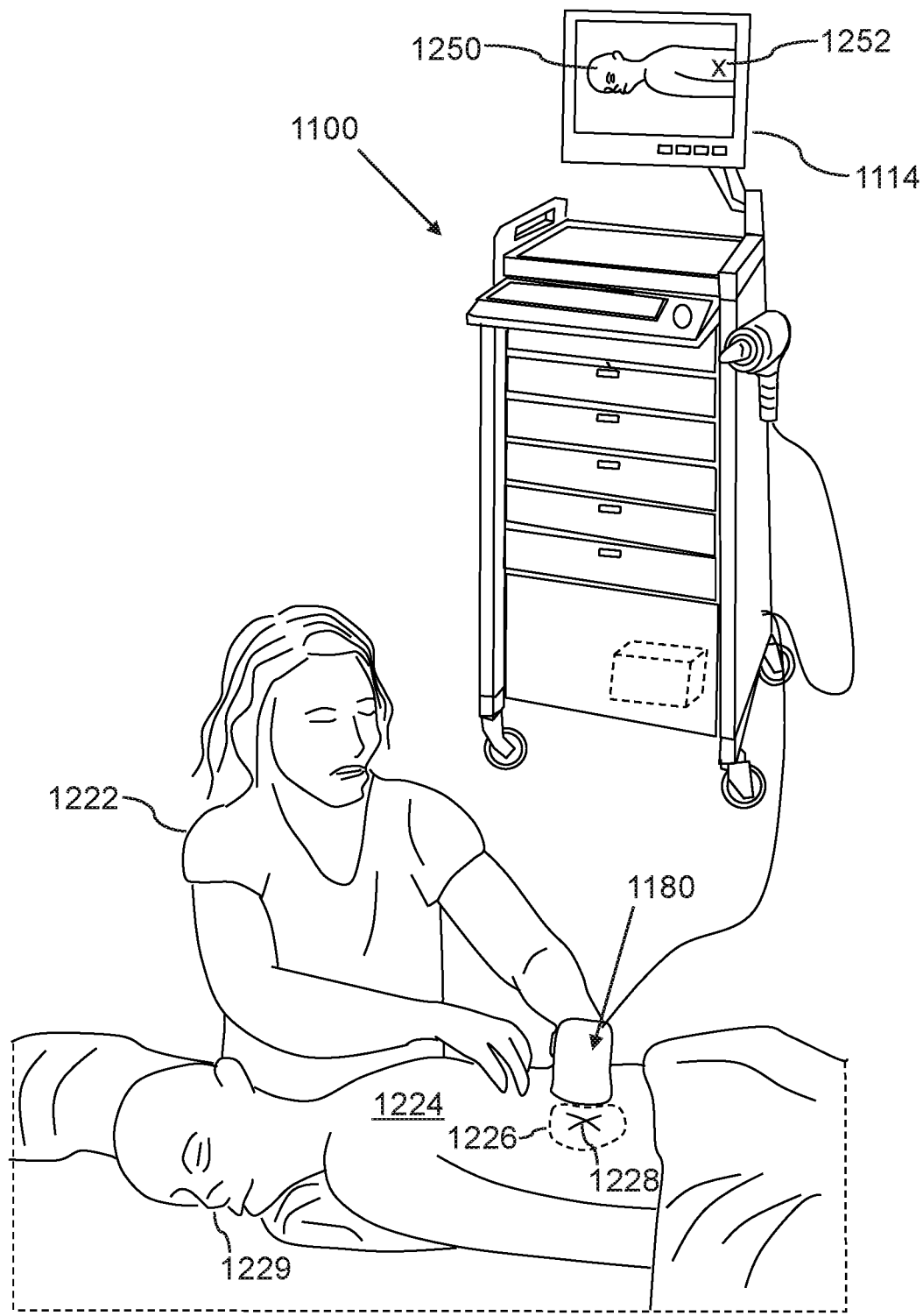
FIG. 2 is a perspective view of a trigger point treatment system in use, according to an embodiment of the invention.
Figure 3:
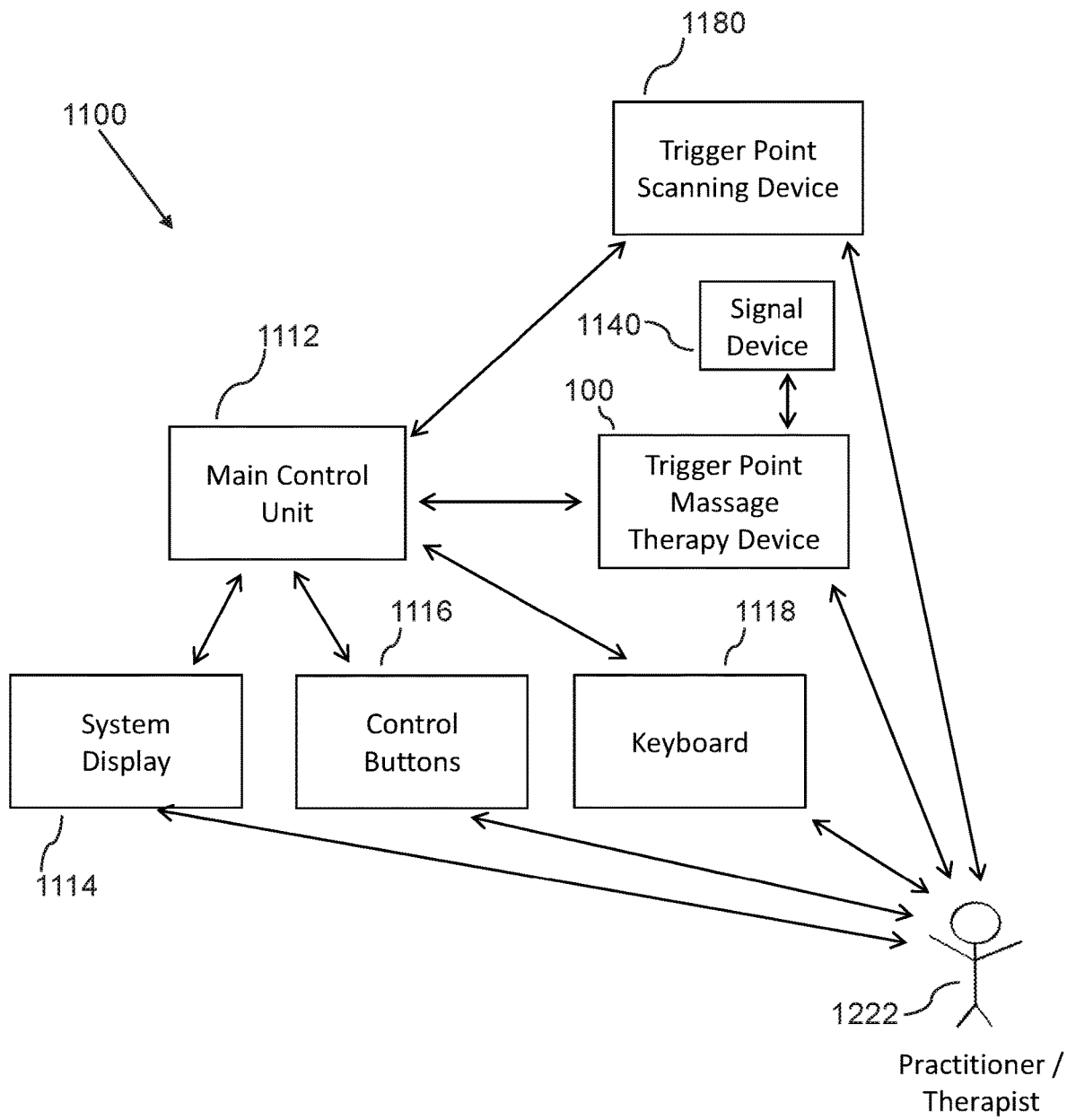
FIG. 3 is a schematic diagram of a trigger point treatment system, according to an embodiment of the invention.
Figure 5:
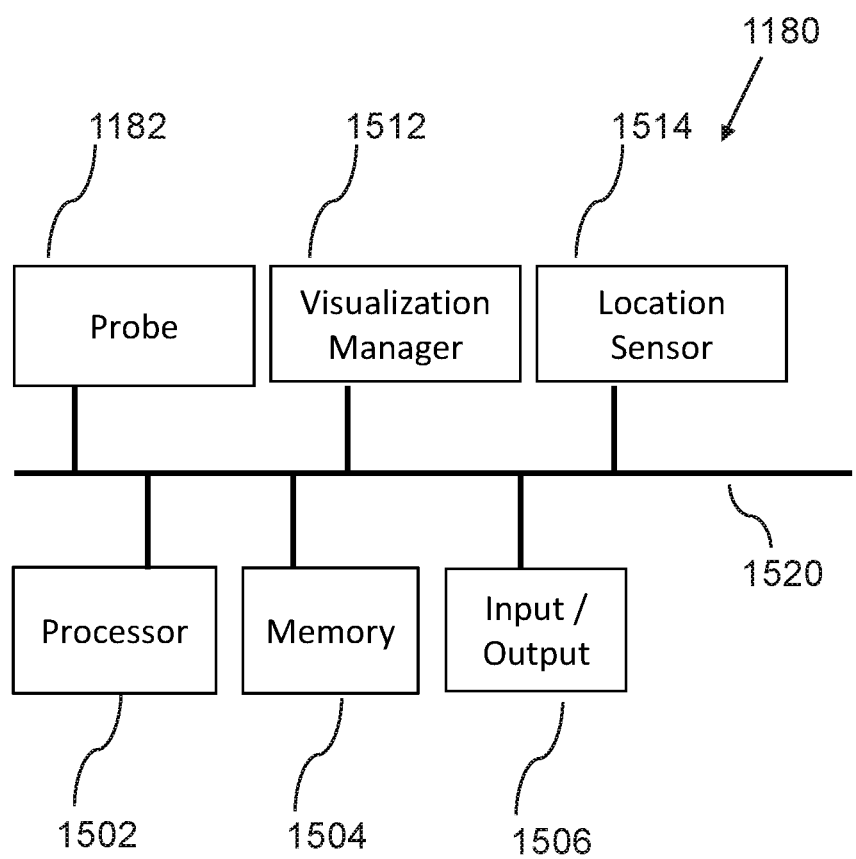
FIG. 5 is a schematic diagram of a trigger point scanning device, according to an embodiment of the invention.

In an embodiment, as shown in FIG. 5, the trigger point scanning device 1180 can include:

a) A processor 1502;

b) A non-transitory memory 1504;

c) An input/output component 1506;

d) a scanning probe 1182, which produces an imaging signal;

e) a visualization manager 1512, which can be configured to process the scanning signal received from the scanning probe, to create a scanning image, such that the scanning image can be transmitted for display on the display 1114, which can be in transmission via the main control unit 1112 or sent directly to the display 1114; and f) a scanner location sensor 1514, which is configured to capture a location of the scanning probe 1182 during a scanning operation; all connected via g) a data bus 1520;

wherein the trigger point massage therapy device is configured to store a plurality of trigger points, with a location and a maximum pressure for each trigger point in the plurality of trigger points;

In a related embodiment, the location sensor 1514, can be calibrated with a physical reference point 1229, as shown in FIG. 2, which for example can be a nose tip 1229 of the patient 1224 (when the patient is positioned in a reference position/pose), such that the location is found as a vector offset from the physical reference point 1229. Positioning on the three-dimensional anatomical model 1250 can then be calculated as the vector offset from a model reference point in the three-dimensional anatomical model 1250. The location sensor 1514 can be configured to determine a location of the scanning probe 1182, for example via use of GPS, wireless or radio triangulation, or combinations of these. The location sensor can for example call services in GOOGLE™ Location Services or IPHONE™ Location Services, or other location API's available in an operation system of the active asset control device 104. Additionally, the location sensor 1514 may incorporate an inbuilt accelerometer or xyz sensor, or combinations of these in order to determine a vector offset from the physical reference point 1229 and can for example call services in GOOGLE™ ARKIT™ to calculate the direction vector.

In another related embodiment, the trigger point massage therapy device 100 can be configured to receive a manual signal from the patient 1224 to indicate that the applied pressure is painful, such that the maximum pressure is the applied pressure when the patient 1224 submits the manual signal, such that the maximum pressure is stored in the trigger point massage therapy device 100 for each trigger point in the plurality of trigger points.

In another related embodiment, the trigger point treatment system 1100 can further include a signal device 1140 (also called a clicker 1140) including a signal button 1142, such that the signal device 1140 is connected to the trigger point massage therapy device 100 via a wired or wireless connection; such that the patient 1224 provides the manual signal by pressing the signal button 1142.

In yet another related embodiment, the trigger point massage therapy device 100 can further include a target pressure indicator 268, which displays a targeted pressure, wherein the targeted pressure is determined as a predetermined proportion of the maximum pressure.

Figure 6:
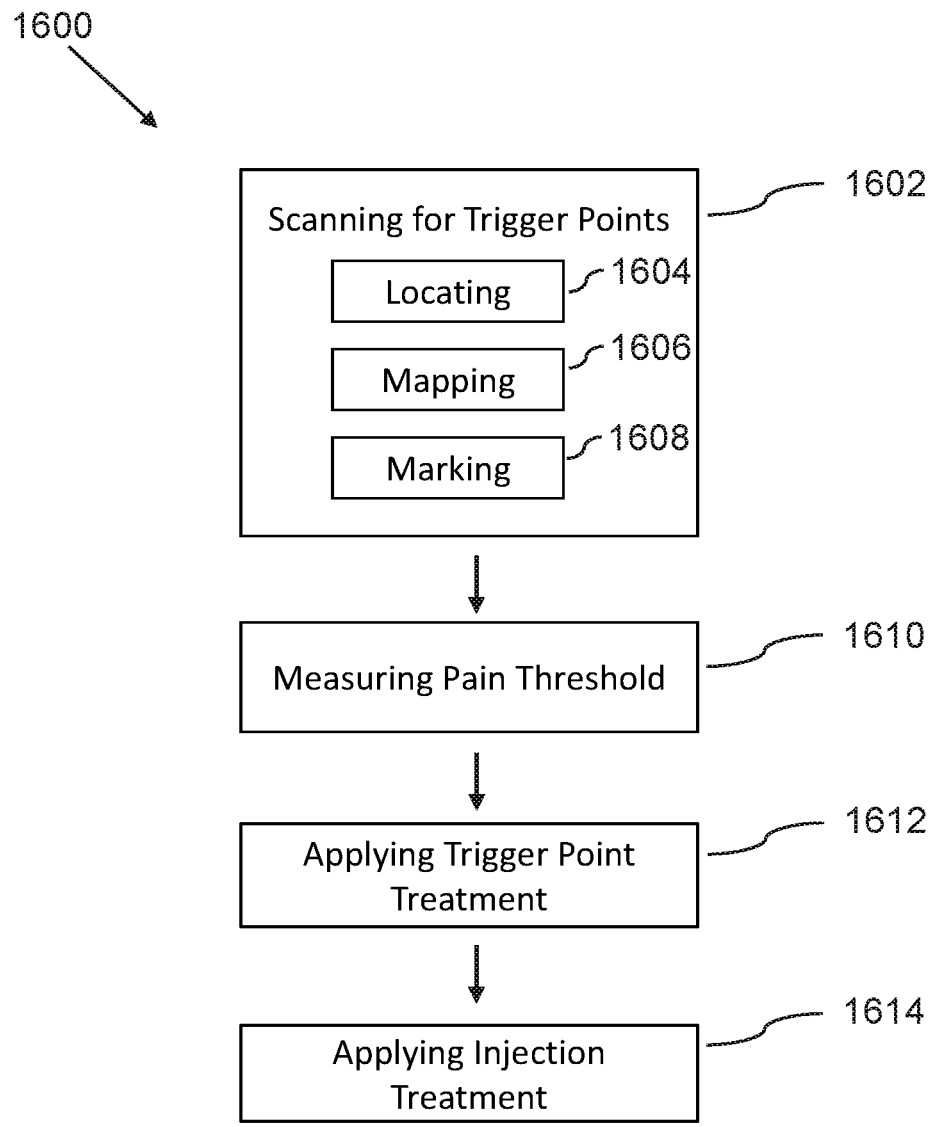
FIG. 6 is a schematic diagram of a trigger point treatment method, according to an embodiment of the invention.

In an embodiment, as shown in FIG. 6, a method of trigger point treatment 1600 for a healthcare practitioner 1222 to treat a patient comprises:

a) scanning for myofascial trigger points 1602, by using a trigger point scanning device 1180, including:

i. locating trigger points 1604 by using the trigger point scanning device 1180 to identify a plurality of trigger points by reviewing scanning images on the display 1114 (in the form of 2D or 3D ultrasound images), wherein the scanning images are received from the trigger point scanning device 1180, such that the plurality of trigger points can be stored in a trigger point storage 1412 of the main control unit 1112;

Locating trigger points 1604 by using the trigger point scanning device 1180 can use well-known methods for detecting trigger points using ultrasound imaging, such as for example described in "Novel Applications of Ultrasound Technology to Visualize and Characterize Myofascial Trigger Points and Surrounding Soft Tissue", Siddhartha Sikdar et al., Arch Phys Med Rehabil, 2009 November; 90(11): 1829-1838.

ii. mapping trigger points 1606, wherein a location is obtained from a scanner location sensor 1514 for each of the trigger points, such that the location is displayed with a location marking 1252 on a three-dimensional anatomical model 1250 shown on the display 1114, as shown in FIG. 2. The three-dimensional anatomical model 1250 can include muscle and body zones; and iii. marking trigger points 1608, wherein each trigger point is marked with a physical marking 1228 on the patient 1224 (i.e. on a skin surface of the patient 1224), as shown in FIG. 2, for example using a marker pen 1186, which can be attached to the trigger point scanning device 1180;

b) measuring a pressure pain threshold 1610 for each located trigger point in the plurality of trigger points by using a trigger point massage therapy device 100, by gradually increasing an actual pressure until the patient submits a manual signal (such as a voice, hand signal, or button press signal) to indicate that the pressure is painful, such that a maximum pressure is the actual pressure when the patient submits the manual signal, such that the maximum pressure is stored in the trigger point massage therapy device 100 for each located trigger point (via an input provided via the input/output component 306);

c) applying a trigger point treatment 1612 for each located trigger point by using a trigger point massage therapy device 100, such that an actual/targeted treatment pressure is applied for each located trigger point as a predetermined proportion of the maximum pressure; in order to deactivate active and latent myofascial trigger points, break up scar tissue, adhesions, connective tissue, pain holding patterns, and muscle spasms. This treatment will be a primary non-invasive treatment. The trigger point treatment 1612 is described in further detail as a trigger point therapy method 1000 below, as shown in FIG. 16. The trigger point massage treatment 1612 can also be referred to as an ischemic compression friction therapy/neuromuscular therapy 1612; and d) (optionally) applying an injection treatment 1614 for each located trigger point by injecting a treatment liquid into each located trigger point. The treatment liquid can for example include saline, local anesthetic, and/or corticosteroid. The trigger point injection functions as an invasive secondary treatment for treating chronic myofascial pain, and can be provided by neurologists, MDs, Nurse Practitioners, and others who are authorized/licensed to administer injections.

In a related embodiment, the predetermined proportion can be 5%, 10%, 20%, 30%, 40%, 50%, 60%, 70%, 80%, 90%, 95%, or 100% of the maximum pressure; or the predetermined proportion can be in a range of 10%-100%, 5%-95%, 10%-95%, 10%-90%, or 20%-90% of the of the maximum pressure; or some other predetermined range combination of these maximum pressure values.

In another related embodiment, the trigger point system can further include a signal device 1140 (also called a clicker 1140) including a signal button 1142, such that the signal device 1140 is connected to the trigger point massage therapy device 100 via a wired or wireless connection; such that during measuring a pressure pain threshold 1610 the patient provides a manual signal to indicate that the pressure is painful by pressing the signal button 1142 of the signal device 1140, such that a maximum pressure is stored in the trigger point massage therapy device 100 for each located trigger point;

In another related embodiment of the method of trigger point treatment 1600, the act of holding the pressure can further include vibrating the pressure point tip.

In a related embodiment, the trigger point massage therapy device 100 can be used to apply ischemic compression pressure treatment, whereby the trigger point massage therapy device 100 provides a trigger point ischemic compression technology system (ICT).

In another related embodiment, the trigger point scanning device 1180 ultrasound imaging scanning probe 1182 to scan trigger points over muscle tissue and musculoskeletal system body zones; scalp; neck; torso; upper and lower back; shoulder; hip; knee; ankle; extremities, such as: hands, arms, leg and feet.

In a further related embodiment, the ultrasound imaging scanning probe 1182 can be configured to provide two-dimensional gray scale imaging, three-dimensional color imaging and/or doppler imaging of trigger points.

In another related embodiment, the main control unit 1112 of the trigger point treatment system 1100 can be configured to provide scanner calibration of the trigger point scanning device 1180 and measuring calibration of the trigger point massage therapy device 100.

In yet another related embodiment, the main control unit 1112 of the trigger point treatment system 1100 can be configured to provide reports and results.

In yet another related embodiment, the main control unit 1112 can further include a patient information manager 1414, which is configured to receive and store input of patient data, including name, date of birth, address, age, sex, phone, Insurance company, insurance ID number phone number, weight, height, pain scale, etc. Data can be input via touch screen 1114, voice recording or key pad 1118, and can include using, computer, laptop, or other computer processing system.

In a related embodiment, trigger points can be located, mapped, and marked in scalp, cervical region, thoracic region, lumbar region, sacral region, upper and lower extremities.

In yet another related embodiment, the trigger point storage 1412 can store the applied pressure as applied by the therapist, such that a permanent record is retained of the pressure sensed by the pressure sensor. The trigger point storage 1412 can further store the plurality of trigger points, each trigger point comprising a location and pressure pain threshold.

In another related embodiment, the trigger point massage therapy device 100 can be used to apply an ischemic compression treatment, using controlled pressure applied with the pressure point tip 122 to the muscle tissue in all body zones: scalp, head, neck, torso, pelvis, hand, legs, wrist, and feet, for treating trigger points.

In a related embodiment, the trigger point scanning device 1180 can include a soft palm pressure pad with a curved contour, and a handle with silicone or rubberized grip points.

In another related embodiment, a surface of the scanning probe 1182 can be made of plastic.

An embodiment of a trigger point massage therapy device 100 describes a handheld device for single hand or dual hand operation that can facilitate well-controlled ischemic compression/trigger point therapy and is suitable for long-term use by massage therapists and other health practitioners, with minimal risk of pain or injury.

In a related embodiment, a health practitioner can apply pressure via one or two-handed operation and can monitor that actual pressure applied is approximately equal to a displayed target pressure.

In a related embodiment, various programs and controls can be selected via an attached control unit.

In related embodiments, the pressure point tip 122 of the trigger point massage therapy device 100 can apply rotation, pulsation, vibration, move forward and backward movement of tip, clockwise, anti-clockwise movement, unwinding, and movements in increments of a predetermined duration, specified in milliseconds.

In the following we describe the structure of such an embodiment in the form of trigger point massage therapy device 100 with reference to FIG. 7, in such manner that like reference numerals refer to like components throughout; a convention that we shall employ for the remainder of this specification.

A trigger point massage therapy device 100 can include
a) A main body 110, which can further include
  i. A soft palm pressure pad 111, which for example can be an overmolded rubber component, to allow a therapist to apply additional pressure with the palm of a second hand.
  ii. A connection pin 112, for example manufactured in metal or other suitable material; and
  iii. A pressure point tip 122, which is connected to the connection pin, for example via snap-lock, screw, or other fastening mechanism, and can be manufactured in a plastic, rubber or silicone material;
b) A handle 102, wherein the handle can be a pistol-type grip or some other ergonomic handle configuration, which can be manufactured in plastic or other suitable material, and can further comprise:
  iv. A soft rear hand grip 106;
  v. A soft front hand grip 108;
  Wherein both the soft rear hand grip 106 and the soft front hand grip 108 for example can be over molded rubber components, which in conjunction enable improved comfort and hold, when gripped by a first hand of the practitioner;
c) A power and control cable 160;
d) A control unit 150, which can be configured to program and control the functions of the trigger point massage therapy device 100, via the control cable 160; and
e) A power cable 130.

In a related embodiment, a pressure point tip can further include a pressure point base 121, which has a main pressure point tip 122, where-on can further be installed, additional pressure point tips 124, 126, 128, of different sizes, which can be manufactured in a rubber material;

In related embodiments, the pressure point tips 122 124 126 128 can be made of materials of different hardness and friction. In some embodiments the pressure point tips 122 124 126 128 can be a soft, medium or hard rubber material.

In alternative embodiments, the pressure point tips 122 124 126 128 can be made of a soft, medium or hard silicone material.

In yet other alternative embodiments, the pressure point tips 122 124 126 128 can be a made from plastic materials, which can be suitable for application where a harder pressure point tip is needed.

In an embodiment, illustrated in FIG. 8, the control unit 150 can include:
a) A start button 256, for starting a therapy session;
b) A stop button 257, for ending a therapy session;
c) A pulse button 251, for switching to the pulse function, which starts a pulsating pattern emitted via the connection pin 112 and transferred to the main pressure point tip 122.
d) A kneading button 252, for switching to the kneading function, which starts a kneading pattern emitted via the connection pin 112 and transferred to the main pressure point tip 122.
e) An unwind button 253, for switching to the unwind function, which starts an unwind pattern, in the form of a counter-clock rotation, emitted via the connection pin 112 and transferred to the main pressure point tip 122.
f) A vibrate button 254, for switching to the vibrate function, which starts a vibration pattern emitted via the connection pin 112 and transferred to the main pressure point tip 122.
g) A function reset button 255, for resetting the selected function to neutral;
h) A trigger point button 258, for switching to the trigger point mode, which selects a trigger point mode adjustment of the selected function pattern 251 252 253 254.
i) A chronic pain button 259, for switching to the chronic pain mode, which selects a chronic pain mode adjustment of the selected function pattern 251 252 253 254.
j) A muscle spasm button 260, for switching to the muscle spasm mode, which selects a muscle spasm mode adjustment of the selected function pattern 251 252 253 254.
k) An acute pain button 261, for switching to the acute pain mode, which selects an acute pain mode adjustment of the selected function pattern 251 252 253 254.
l) A mode reset button 262, for resetting the selected mode to neutral;
m) A pressure indicator 265, further including:
  i. An actual pressure indicator 266, which displays the current actual pressure, for example on a relative scale from 0 to 100, as applied by a therapy practitioner.
  ii. A pressure status graph indicator 267, which displays a historical graph of the pressure applied in the last X seconds, and a planned graph of the pressure targeted or planned by the selected settings to be applied in the next X seconds. X is a predetermined value, which for example can be 60 seconds.
  iii. A target pressure indicator 268, which displays the pressure currently targeted or planned, in accordance with selected settings.
n) A time increase button 270, for lengthening the treatment time;
o) A time decrease button 272, for shortening the treatment time;
p) An intensity increase button 275, for increasing the treatment intensity;
q) An intensity lowering button 277, for decreasing the treatment intensity;
r) A program select button 280, for cycling through a plurality of pre-determined programs;
s) A firm pressure button 281, for selecting the firm pressure function, which can increase the pressure in time-intervals of a predetermined number of milliseconds, via outward movement of the connection pin 112;
t) An unwind button 282, for selecting the unwind function, which initiates a counter clock-wise unwind rotation to relax the trigger point muscles;
u) A vibrate button 283, for selecting the vibrate function;
v) A light program adjustment button 285, for selecting a light intensity program, wherein the targeted pressure, as indicated on the pressure status graph indicator 267 and the target pressure indicator 268 is gradually increased from zero for 3 seconds, and then maintained for 5 seconds;
w) A low program adjustment button 286, for selecting a low intensity program, wherein the targeted pressure, as indicated on the pressure status graph indicator 267 and the target pressure indicator 268 is gradually increased from zero for 5 seconds, and then maintained for 10 seconds;
x) A medium program adjustment button 287, for selecting a medium intensity program, wherein the targeted pressure, as indicated on the pressure status graph indicator 267 and the target pressure indicator 268 is gradually increased from zero for 7 seconds, and then maintained for 14 seconds;
y) A deep program adjustment button 288, for selecting a deep intensity program, wherein the targeted pressure, as indicated on the pressure status graph indicator 267 and the target pressure indicator 268 is gradually increased from zero for 10 seconds, and then maintained for 20 seconds.

In an embodiment, illustrated in FIG. 9, the main body 110 can include the following internal components:
a) A processor 302;
b) A memory 304;
c) An input/output component 306;
d) An axle 330, which is connected to the connection pin 112;
e) A step-vibration component 310, which can be configured to produce a vibration and longitudinal movement of the axle 330, wherein an outward movement can momentarily increase the pressure, such that a sequence of outward movement steps, in increments of a predetermined duration, specified in milliseconds, can increase the pressure in increments, and a sequence of inward movements can similarly decrease the pressure;

f) A pressure sensor component 311, which is connected to the axle 330, such that the pressure sensor component 311 can measure a pressure applied to the pressure point tip, which is transmitted via the connection pin 112 and the axle 330, so that the axle 330 applies the transmitted pressure to the pressure sensor component 311;

g) An electro-motor 312, which can be configured to rotate the axle 330, both clockwise and counter-clockwise, under control by the processor 302;

h) A heating component 314, which can heat the connection pin 112, whereby attached tips can be heated;

i) An ultrasound component 316, which can target the treatment area 1226 with ultrasound applied close to the treatment tip connected to the connection pin 112, and radiated either via an ultrasound aperture in the surface of the main body 110, or via the axle 330 and the connection pin 112;

j) An infrared component 318, which can radiate the treatment area 1226 with infrared radiation targeting the area close to the treatment tip connected to the connection pin 112, and radiated via an infrared aperture in the surface of the main body 110;

k) An electrical stimulation component 320, which can stimulate the treatment area 1226 with electrical stimulation targeting the area close to the treatment tip connected to the connection pin 112, and transmitted via the axle 330 and the connection pin 112; and l) A cold laser light component 322, which can radiate the treatment area 1226 with cold laser light targeting the area close to the treatment tip connected to the connection pin 112, and radiated via a cold laser light aperture in the surface of the main body 110; wherein all components are connected via m) A data bus 340.

In various embodiments, the trigger point massage therapy device 100 can be manufactured in consumer, prosumer/semi-professional, and professional variants for use in both home and clinical environments.

In a related embodiment, the step-vibration component 310 can be connected to a frame 360 of the main body 110, via a frame connection 350, in order to transmit pressure/force applied by a user of the trigger point massage therapy device 100.

In a related embodiment, the pressure sensor 311 can be connected to a frame 360 of the main body 110, via a frame connection 350, in order to transmit pressure/force applied by a user of the trigger point massage therapy device 100.

In FIG. 9, the pressure sensor 311 is shown connected indirectly to the frame 360, via the step-vibration component 310. In alternative embodiments, the step-vibration component 310 can be connected indirectly to the frame 360, via the pressure sensor 311, or both the step-vibration component 310 and the pressure sensor 311 can be connected directly to the frame 360.

In a related embodiment, the electro-motor 312 can be connected to a frame 360 of the main body 110, via a frame connection 350, in order to rotate the axle 330 relative to the frame 360 of the main body 110.

In a related embodiment, the handle 102 can be connected to the frame 360 of the main body 110.

In a related embodiment, an outward step of the step-vibration component 310 can cause an outward movement of the axle in a range of 0.5 mm to 5 mm. Similarly, an inward step of the step-vibration component 310 can cause an inward movement of the axle in a range of 0.5 mm to 5 mm. Depending on the application, these ranges can be larger or smaller.

In a related embodiment, the step-vibration component 310 can be a linear actuator, for example based on a piezoelectric or electro-mechanical design, such that the step-vibration component is further configured with an electro-mechanical vibrator.

In a further related embodiment, the linear actuator of the step-vibration component 310 can be configured with a step motor.

In a related embodiment, the connection pin 112 can be an integral part of the axle 330, such that the connection pin 112 is part of an outer end of the axle 330.

In various embodiments, the trigger point massage therapy device 100, can also function as and be referred to as a neuromuscular therapy device.

In various related embodiments, the pressure sensor component 311 can be an electronic pressure sensor, including well-known pressure sensors, such as piezo-resistive strain gauges, capacitive, electromagnetic, piezoelectric, or optical pressure sensors.

In various embodiments, a pressure point tip 122 124 126 128 can range in size from ⅛" to 3", and be available in a plurality of incremental sizes.

Figure 10:
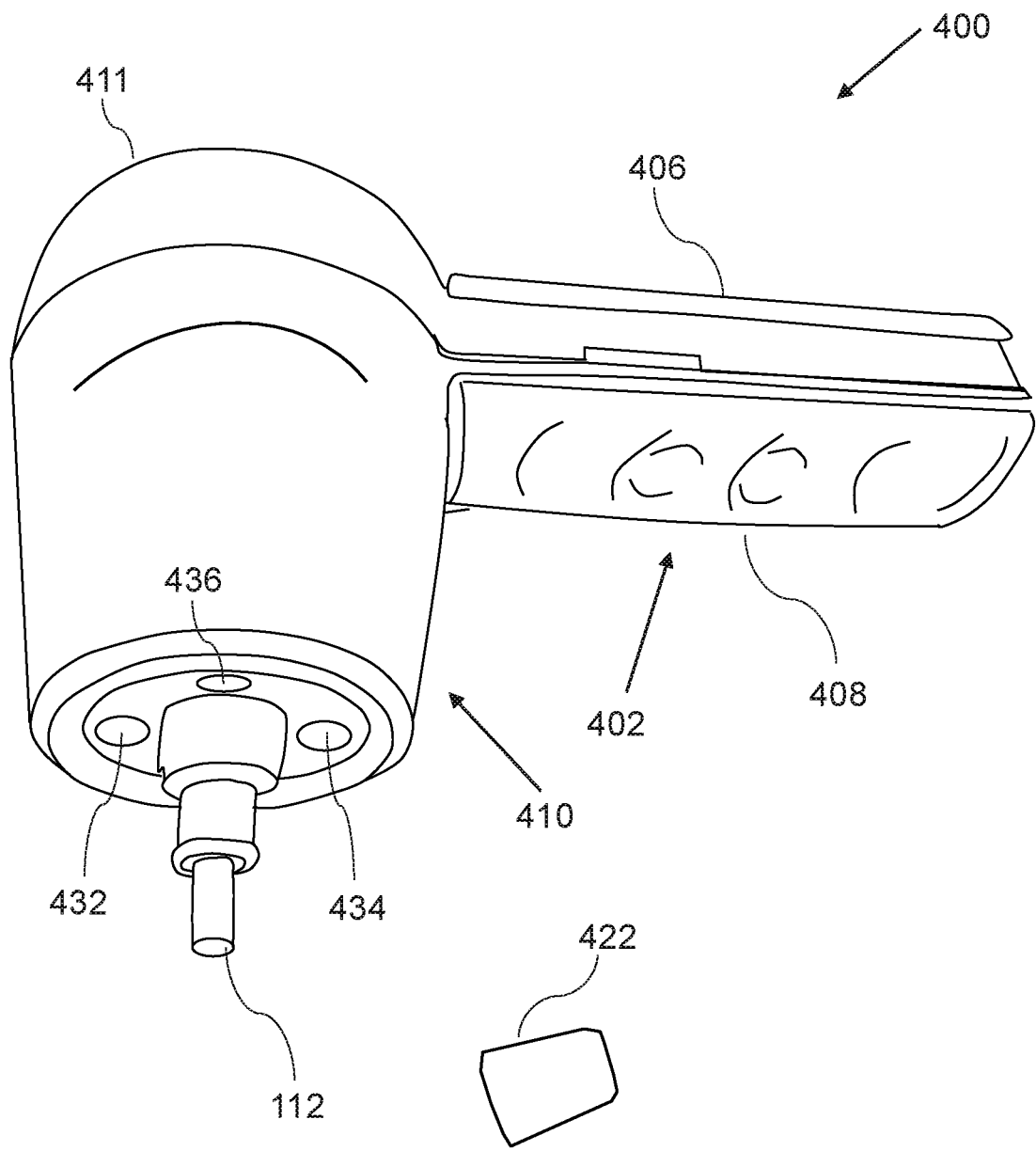
FIG. 10 is a front perspective view of a trigger point massage therapy device, according to an embodiment of the invention.

In an embodiment, FIG. 10 shows a front perspective view of an alternative design for a trigger point massage therapy device 400, comprising:

a) A main body 410, including
  i. A soft palm pressure pad 411,
  ii. A connection pin 112; and
  iii. A pressure point tip 422; and b) A handle 402, further including:
  i. A soft rear hand grip 406; and
  ii. A soft front hand grip 408.

In a related embodiment, FIG. 10 illustrates a location for an ultrasound aperture 432, for radiating ultrasound from the ultrasound component 316.

In a related embodiment, FIG. 10 illustrates a location for an infrared aperture 434, for emitting infrared radiation from the infrared component 318.

In a related embodiment, FIG. 10 illustrates a location for a cold laser light aperture 436, for emitting infrared radiation from the infrared component 318.

In a related embodiment, the pressure point tip 422 can be configured with a slide-on fastening mechanism, such that the pressure point tip 422 slides on to the connection pin 112, such that the pressure point tip 422 is held in place by a sufficiently tight grip from friction between the connection pin 112 and an inner surface of the pressure point tip 422.

In another related embodiment, the pressure point tip 422 can be configured with a screw cap fastening mechanism, to secure the pressure point tip 422 on the connection pin 112.

Figure 11:
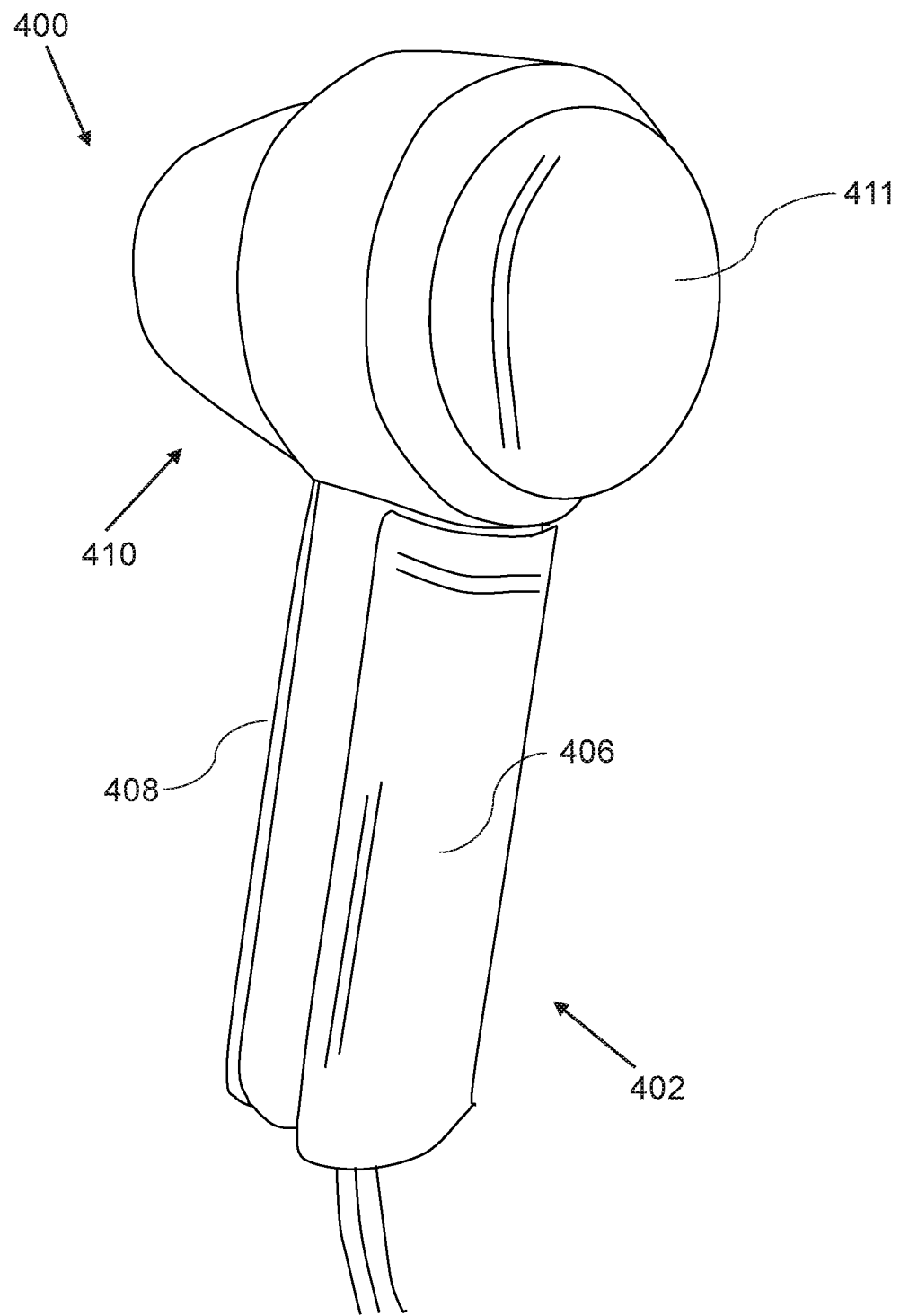
FIG. 11 is a rear perspective view of a trigger point massage therapy device, according to an embodiment of the invention.

FIG. 11 shows a rear perspective view of the trigger point massage therapy device 400.

Figure 12:
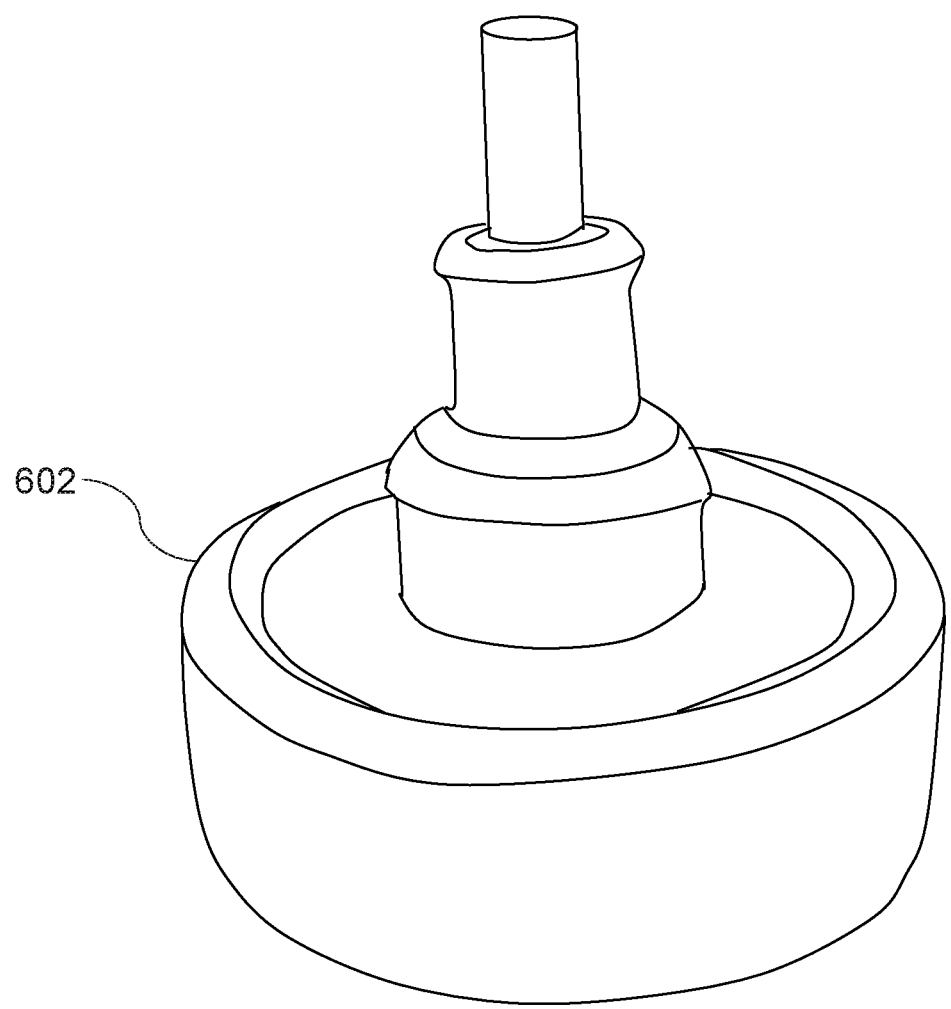
FIG. 12 is a perspective view of a front cover for a trigger point massage therapy device, according to an embodiment of the invention.

In a related embodiment, the trigger point massage therapy device 400, can further include a front cover 602, as shown in FIG. 12, which can protect a front of the main body 410 from dust and moisture, such that it covers the front, and the connection pin, such that the pressure point tip 422 (shown in FIG. 10) is mounted on the front cover 602, such that the front cover 602, is sufficiently thin and flexible to transmit pressure and vibrations. The front cover 602 can further include apertures to align with the ultrasound, infrared, and cold laser light apertures 432 434 436.

In a further related embodiment, the front cover 602 can be manufactured from a medical grade silicone rubber configured as a molded sheet with a thickness in a range from 0.25-2 mm.

Figure 13:
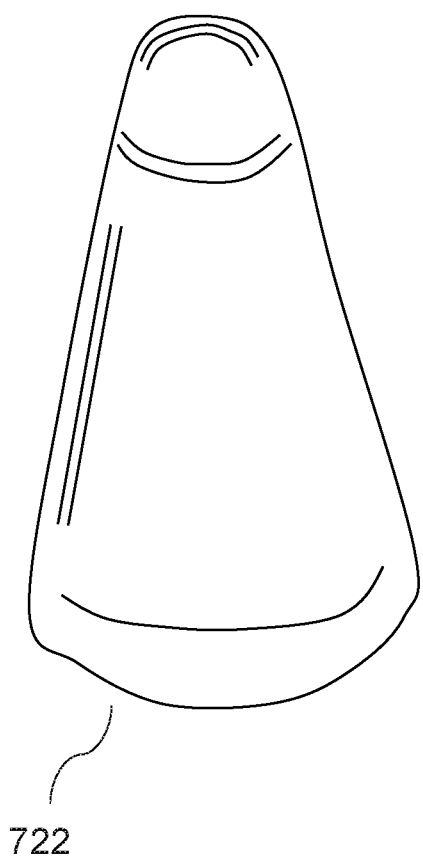
FIG. 13 is a top perspective view of a pressure point tip for a trigger point massage therapy device, according to an embodiment of the invention.
Figure 14:
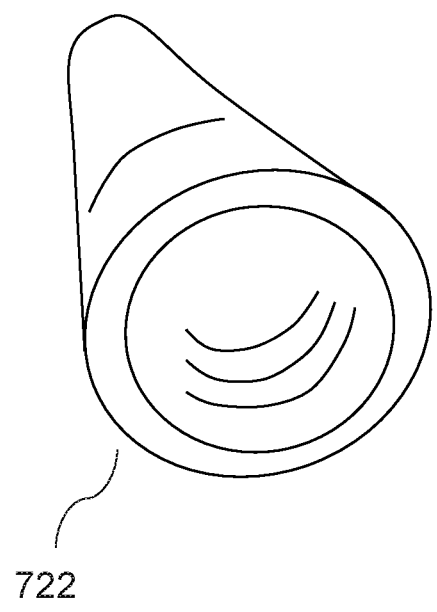
FIG. 14 is a bottom perspective view of a pressure point tip for a trigger point massage therapy device, according to an embodiment of the invention.

In a related embodiment, FIG. 13 and FIG. 14 show respectively a front and a rear perspective view of a pressure point tip 722 made from a medical grade silicone rubber.

In a related embodiment, the trigger point massage therapy device 400 can be made with a two-tone color scheme in white and grey, with silicone pressure point tips 722 made in a grey color.

Figure 15:
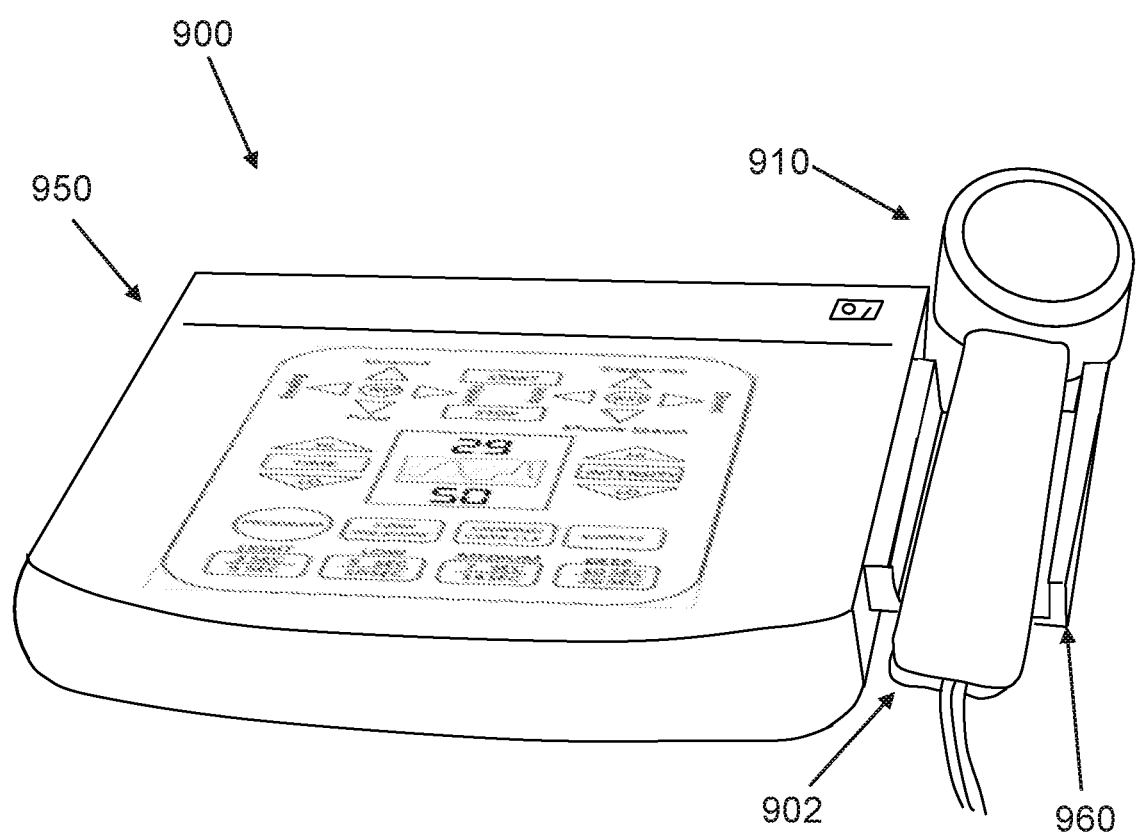
FIG. 15 is a perspective view of a trigger point massage therapy device, according to an embodiment of the invention.

In an alternative embodiment, FIG. 15 shows a desktop version of a trigger point massage therapy device 900, with a control unit 950, configured to be mounted on a table or cart surface, such that a handheld main body 910 with a handle 902 can be mounted on a side of the control unit 950, for example such that the handle 902 can rest on a hook or cradle 960, which is mounted to a side of the control unit 950.

In an embodiment, a trigger point therapy method can include:
 a) Sensing pressure applied by a therapist;
 b) Holding the pressure; and
 c) Increasing the pressure; while simultaneously or sequentially:
   i. Rotating slowly a pressure point tip clock-wise or counter-clock-wise;
   ii. Vibrating the pressure point tip.

In an embodiment, a trigger point therapy method 1000, as shown in FIG. 16, can include:
 a) measuring pressure 1002, wherein a pressure is applied by a therapist using a pressure point applied to a treatment area 1226, such that the pressure is measured with a pressure sensor during application of the pressure;
 b) adjusting the pressure 1004, wherein the pressure is adjusted by the therapist, until the pressure reaches a predetermined target pressure value;
 c) holding the pressure 1006, wherein the pressure at the target value for a predetermined length of time; while simultaneously or sequentially:
   i. Rotating the pressure point tip 1007 clock-wise or counter-clock-wise;
   ii. Vibrating the pressure point tip 1008; and
 d) Increasing the pressure 1010, wherein the pressure is increased in increments.

FIGS. 3, 4, 5, 6, 9, and 16 are block diagrams and flowcharts, methods, devices, systems, apparatuses, and computer program products according to various embodiments of the present invention. It shall be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, FIGS. 3, 4, 5, and 9 depict the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer can include a processing unit and a system memory, which may include random access memory (RAM) and read-only memory (ROM). The computer also may include nonvolatile storage memory, such as a hard disk drive, where additional data can be stored.

It shall be understood that the above-mentioned components of the main control unit 1112, the trigger point scanning device 1180, and the trigger point massage therapy device 100 are to be interpreted in the most general manner.

For example, the processors 1402 1502 302 can each respectively include a single physical microprocessor or microcontroller, a cluster of processors, a datacenter or a cluster of datacenters, a computing cloud service, and the like.

In a further example, the non-transitory memories 1404 1504 304 can each respectively include various forms of non-transitory storage media, including random access memory and other forms of dynamic storage, and hard disks, hard disk clusters, cloud storage services, and other forms of long-term storage. Similarly, the input/output components 1406 1506 306 can each respectively include a plurality of well-known input/output devices, such as screens, keyboards, pointing devices, motion trackers, communication ports, and so forth.

Furthermore, it shall be understood that the main control unit 1112, the trigger point scanning device 1180, and the trigger point massage therapy device 100 can each respectively include a number of other components that are well known in the art of general computer devices, and therefore shall not be further described herein. This can include system access to common functions and hardware, such as for example via operating system layers such as WINDOWS™, LINUX™, and similar operating system software, but can also include configurations wherein application services are executing directly on server hardware or via a hardware abstraction layer other than a complete operating system.

An embodiment of the present invention can also include one or more input or output components, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

The many features and advantages of the invention are apparent from the detailed specification, and thus, it is intended by the appended claims to cover all such features and advantages of the invention, which fall within the true spirit and scope of the invention.

For example, alternative embodiments can reconfigure or combine the computational components of the main control unit 1112, the trigger point scanning device 1180, and the trigger point massage therapy device 100. Parts or all of the computational components of the main control unit 1112 can be configured to operate in the trigger point scanning device 1180 and/or the trigger point massage therapy device 100. Alternatively, parts or all of the computational components of the trigger point scanning device 1180 and/or the trigger point massage therapy device 100 can be configured to operate in the main control unit 1112.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. A trigger point treatment system for treating a patient, the trigger point treatment system comprising:
   a) a system body, comprising:
      a display;
   b) a trigger point scanning device, which is connected to the system body, the trigger point scanning device comprising:
      a scanning probe, such that the scanning probe is configured to receive a scanning signal from a treatment area of the patient, such that the trigger point scanning device processes the scanning signal to generate a scanning image, which is transmitted to the display; and
   c) a trigger point massage therapy device, comprising:
      a pressure point tip;
      a pressure sensor component, which is connected to the pressure point tip, such that the pressure sensor component measures a pressure applied to the pressure point tip;
      an actual pressure indicator, which displays a current actual pressure, obtained in communication with the pressure sensor component;
      wherein the trigger point massage therapy device is configured to store a plurality of trigger points, with a location and a maximum pressure for each trigger point in the plurality of trigger points;
      whereby a therapist applies an applied pressure to the treatment area of the patient via the pressure point tip, such that the therapist adjusts the applied pressure via observation of the current actual pressure on the actual pressure indicator;
      wherein the trigger point massage therapy device is configured to receive a manual signal from the patient to indicate that the applied pressure is painful, such that the maximum pressure is the applied pressure when the patient submits the manual signal, such that the maximum pressure is stored in the trigger point massage therapy device for each trigger point in the plurality of trigger points;
      wherein the trigger point massage therapy device further comprises a target pressure indicator, which displays a targeted pressure, wherein the targeted pressure is determined as a predetermined proportion of the maximum pressure, wherein the predetermined proportion is in a range of 5%-95%.

2. The trigger point treatment system of claim 1, further comprising a signal device, which comprises a signal button; such that the signal device is connected to the trigger point massage therapy device; such that the patient provides the manual signal by pressing the signal button.

3. The trigger point treatment system of claim 1, wherein the scanning probe is an ultrasound imaging scanning probe.

4. The trigger point treatment system of claim 1, wherein the system body further comprises a main control unit, comprising:
   a) a processor;
   b) a non-transitory memory;
   c) an input and output component;
   d) a control manager, which is configured to communicate with and control operation of the trigger point scanning device and the trigger point massage therapy device; and
   e) a trigger point storage, which is configured to store the plurality of trigger points, with the location and the maximum pressure for each trigger point in the plurality of trigger points; wherein the processor, non-transitory memory, input and output component, control manager, and trigger point storage are all connected via
   f) a data bus.

5. The trigger point treatment system of claim 1, wherein the trigger point scanning device further comprises:
   a) a processor;
   b) a non-transitory memory;
   c) an input and output component; and
   d) a visualization manager, which is configured to process the scanning signal received from the scanning probe, to create the scanning image, such that the scanning image is transmitted to the display; wherein the processor, non-transitory memory, input and output component, and visualization manager are all connected via
e) a data bus.

6. A method of trigger point treatment for a healthcare practitioner to treat a patient, the method of trigger point treatment comprising:
providing a system body, comprising: a display;
providing a trigger point scanning device, which is connected to the system body, the trigger point scanning device comprising:
a scanning probe, such that the scanning probe is configured to receive a scanning signal from a treatment area of the patient, such that the trigger point scanning device processes the scanning signal to generate a scanning image, which is transmitted to the display; and
providing a trigger point massage therapy device, comprising:
a pressure point tip;
a pressure sensor component, which is connected to the pressure point tip, such that the pressure sensor component measures a pressure applied to the pressure point tip;
an actual pressure indicator, which displays a current actual pressure, obtained in communication with the pressure sensor component;
scanning for myofascial trigger points by using the trigger point scanning device, wherein scanning for myofascial trigger points comprises:
locating trigger points by using the trigger point scanning device to identify the plurality of trigger points on the patient,
reviewing scanning images on the display, wherein the scanning images are received from the trigger point scanning device;
mapping trigger points, wherein a location is obtained from the scanning probe of the trigger point scanning device for each trigger point in the plurality of trigger points;
storing a plurality of the trigger points, with a location and a maximum pressure for each one of the trigger points in the plurality of trigger points;
applying an applied pressure to the treatment area of the patient via the pressure point tip, wherein the pressure is applied by a therapist;
measuring the applied pressure, such that the pressure is measured with the pressure sensor component during application of the pressure, and adjusting the applied pressure via observation of the current actual pressure on the actual pressure indicator, wherein the pressure is adjusted by the therapist;
measuring a pressure pain threshold for each of the trigger points in the plurality of trigger points by gradually increasing the actual pressure until the patient submits a manual signal to indicate that the actual pressure is painful, such that a maximum pressure is the actual pressure when the patient submits the manual signal, such that the maximum pressure is stored in the trigger point massage therapy device for each located trigger point of the plurality of trigger points;
wherein the trigger point massage therapy device further comprises a target pressure indicator, which displays a target pressure, wherein applying the trigger point treatment further comprises that the target pressure is applied for each of the located trigger points as a predetermined proportion of the maximum pressure; wherein the predetermined proportion is in a range of 5%-95%.

7. The method of trigger point treatment of claim 6, wherein the patient submits the manual signal by pressing a signal button of a signal device;
wherein the signal device is connected to the trigger point massage therapy device.

8. The method of trigger point treatment of claim 6 wherein the location is displayed with a location marking on an anatomical model shown on the display.

9. The method of trigger point treatment of claim 6, wherein scanning for myofascial trigger points further comprises:
marking trigger points, wherein each trigger point in the plurality of trigger points is marked with a physical marking on the patient.

10. The method of trigger point treatment of claim 6,
wherein the trigger point treatment comprises:
wherein the pressure is adjusted by the therapist, until the pressure reaches the target pressure; and c) holding the pressure, wherein the pressure is at the target pressure for a predetermined length of time.

11. The method of trigger point treatment of claim 10, wherein holding the pressure further comprises rotating the pressure point tip.

12. The method of trigger point treatment of claim 6, further comprising:
applying an injection treatment for at least one trigger point in the plurality of trigger points by injecting a treatment liquid into the at least one trigger point.

* * * * *